United States Patent [19]
Burstein

[11] Patent Number: 4,847,290
[45] Date of Patent: Jul. 11, 1989

[54] DELTA 1-THC-7-OIC ACID AND ANALGESIC AND ANTI-INFLAMMATORY AGENTS

[76] Inventor: Sumner Burstein, 6 Knight Rd., Framingham, Mass. 01701

[21] Appl. No.: 86,274

[22] Filed: Aug. 17, 1987

[51] Int. Cl.<sup>4</sup> .............................................. A61K 31/35
[52] U.S. Cl. ................................... 514/454; 514/455
[58] Field of Search .............................. 514/454, 455

[56] References Cited

PUBLICATIONS

Burstein, S. et al., *Biochemical Pharmacology*, 35:2553–2558, 1986.
Burstein, S. et al., *Experientia*, 43:402–403, 1987.
Sophia, R. D. et al., *The Journal of Pharmacology and Experimental Therapeutics*, 186:646–655, 1973.
Sophia, R. C. et al., *Pharmacology*, 17:79–82, 1978.
Watanabe, K. et al., *European Journal of Pharmacology*, 63:1–6, 1980.
Widman et al., Metabolism of Delta-1-Tetrahydrocannabinol in Man, in: *Pharmacokinetics and Pharmacodynamics of Psychoacive Drugs*, Eds. G. Barnett and C. N. Chiang, Biomed. Publ., Forest City, California, 1985.
Perez-Reyes, M. Pharmacodynamics of Certain Drugs of Abuse, in: *Pharmacokinetics and Pharmacodynamics of Psychoactive Drugs*, Eds. G. Barnett and C. N. Chiang, Biomed. Publ., Forest City, California, 1985.

*Primary Examiner*—Stanley J. Friedman
*Attorney, Agent, or Firm*—Hamilton, Brook, Smith & Reynolds

[57] ABSTRACT

A non-psychoactive metabolite of THC is described. The invention is based on the discovery that this metabolite has analgesic and anti-inflammatory properties. The use of the metabolite as a therapeutic agent is based upon the further discovery that it is non-ulcerogenic.

8 Claims, No Drawings

DELTA 1-THC-7-OIC ACID AND ANALGESIC AND ANTI-INFLAMMATORY AGENTS

GOVERNMENT SUPPORT

Work described herein was supported in part by Grants DA02043 and DA02052 from the National Institute on Drug Abuse.

BACKGROUND OF THE INVENTION $\Delta^1$-Tetrahydrocannabinol (THC) (Formula I) is the major psychoactive constituent of marijuana (Hollister, L.E. *Science,* 172:21–29, 1971; Isbell, H., Gorodetsky, C. W., Jasinski, D., Claussen, V., von Spulak, F. and Korte, F. *Psychopharmacologia,* 11:184–188, 1967; Mechoulam, R., *Science,* 168:1159–1166, 1970). The initial metabolites of THC are monohydroxy derivatives active as mood-altering agents. It is believed that these monohydroxy derivatives of THC contribute to the overall effects of the drug, but their presence is not required for the psychotropic action of cannabis (Harvey, D. J. and Paton, W. D. M. *Rev. Biochem. Toxic.* 6:250, 1984).

Metabolism of the monohydroxy THC derivatives involves a series of oxidative transformations that ultimately leads to a group of carboxyl-containing derivatives of the parent substance. These acidic metabolites were thought to display none of the biological activities of their precursors and have been generally regarded as inactive metabolic end-products. The most abundant member of this group is the cannabinoid $\Delta^1$-THC-7-oic-acid (Formula II). When tested in humans as well as in the rhesus monkey, this cannabinoid did not show the behavioral activity or the cardiovascular effects characteristic of the parent substance, THC. (Perez-Reyes, M. In: *Pharmacokinetics and Pharmacodynamics of Psychoactive Drugs,* Barnett, G. and Chiang, N. (eds), Biomedical Press, 1985, pages 287–310; Mechoulam, R. and Edery, M. In: *Marijuana,* Mechoulam, R. (ed.), Academic Press, New York, 1973). Thus, little attention has been given to the possible pharmacodynamic properties of this metabolite or any of the other acid metabolites of THC.

Tetrahydrocannabinol ($\Delta^1$-THC)  Formula I

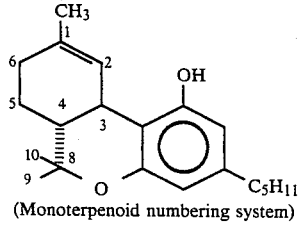

(Monoterpenoid numbering system)

$\Delta^1$-THC-7-OIC-ACID  Formula II

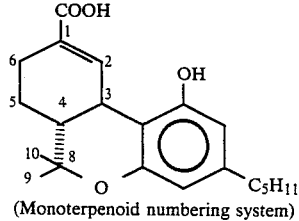

(Monoterpenoid numbering system)

It has long been known that THC possesses potent analgesic and anti-inflammatory properties. However, the biochemical bases for these effects was not well understood. Although it has been suggested that the THC-induced elevation of plasma corticosteroids was responsible, the experimental support for this hyopthesis is inconclusive (Sophia, R. D., Nalepa, S. D., Harakal, J. J. and Vassar, H. B., *J. Pharma. Exper. Ther.* 186:646–655, and 1973). It has also been shown, in a variety of models that $\Delta^1$-THC-7-oic-acid can be a potent inhibitor of the prostaglandin synthetase system (Burstein, S., Hunter, S. A., Lathan, V. and Renzulli, L., *Biochem. Pharmac.* 35:2553–2558, 1986).

The $\Delta^1$-THC-7-oic-acid metabolite has also been shown to antagonize the in vitro action of the parent substance (Burstein, S., Hunter, S. A., Latham, V. and Renzulli, L. *Biochem. Pharmac.* 35: 2553–2558, 1986). The system in which this observation was made involved exposing cells in culture to cannabinoids and measuring the change brought about in the metabolism of arachidonic acid (Burstein, S., Hunter, S. A. and Ozman, K. *Molec. Pharmac.* 23:121, 1983; Burstein, S. and Hunter, S. A. *J. Clin. Pharmac.* 21:2405, 1981; Burstein, S. Hunter, S. A., Sedor, C. and Shulman, S. *Biochem. Pharmac.* 31:2361, 1982). The addition of the metabolite to the culture medium prior to THC exposure resulted in a dramatic lowering of the stimulatory effect of THC on prostaglandin synthesis. A kinetic and chromatographic analysis of the metabolic products in the media suggested that cycloxygenase may be the site of inhibition by the $\Delta^1$-THC-7-oic acid (Burstein, S. et al., *Biochem. Pharmac.* 35:2553–2558, 1986).

SUMMARY OF THE INVENTION

This invention is based on the discovery that $\Delta^1$-THC-7-oic-acid is a potent analgesic and anti-inflammatory agent, and that when administered directly into the stomach is non-ulcerogenic. As a result, this non-psychoactive metabolite of THC can be used as a therapeutic agent for such purposes as the treatment of chronic pain and tissue inflammation often associated with illnesses such as rheumatoid arthritis.

DETAILED DESCRIPTION OF THE INVENTION

The subject invention concerns a non-psychoactive metabolite of THC, $\Delta^1$-THC-7-oic-acid, which has been shown to be an active analgesic and anti-inflammatory agent. The invention is further related to the use of this metabolite as a therapeutic agent in the treatment of pain and tissue inflammation, especially that associated with long-term illnesses such as rheumatoid arthritis. It has been shown that this metabolite does not induce the gastrointestinal damage which accompanies the habitual use of the leading analgesics and nonsteroidal anti-inflammatory agents (NSAIDS) available today.

It has now been discovered that this metabolite, when administered to laboratory animals in a standard pharmacological assay for analgesia (see exemplification), produces a pain-relieving effect which is merely equivalent to that of naproxen (6-Methoxy-$\alpha$-methyl-2-naphthaleneacetic acid), a popular analgesic and anti-inflammatory agent in use today. Thus, the therapeutic effects of the $\Delta^1$-THC-7-oic-acid metabolite can be separated from the psychoactive effects of THC, the parent substance. For the purposes of the present invention, $\Delta^1$-THC-7-oic-acid includes the metabolite having the structure shown in Formula II and all functional equivalents thereof.

One common adverse effect of the consumption of NSAIDS is gastrointestinal damage, generally as bleeding and/or frank ulceration. A frank ulcer is a necrotic lesion, usually elongated, which penetrates the gastric mucosa and resists removal by wiping or rinsing with physiological saline. The therapeutic agent of this invention is non-ulcerogenic. In a standard pharmacological assay for ulcerogenicity it was discovered that the $\Delta^1$-THC-7-oic-acid metabolite did not induce ulcer formation. That is, its administration directly into the stomach did not result in ulcer formation in any rats to which it was given. This result is in sharp contrast to the effects of aspirin which, when given in half the therapeutic dose, induced the formation of gastric lesions in each test animal.

$\Delta^1$-THC-7-oic-acid, which is a non-psychoactive metabolite of THC, has been shown to retain the analgesic and anti-inflammatory properties of THC and to be non-ulcerogenic. This metabolite is especially useful as a therapeutic agent in the treatment of chronic pain and inflammation associated with long-term illnesses, such as rheumatoid arthritis, in which individuals must consume needed drugs over extended periods of time. $\Delta^1$-THC-7-oic-acid produces the desired analgesic and anti-inflammatory effects without subjecting the individual to the risk of developing gastric ulcers, as occurs during habitual consumption of presently available drugs (e.g., aspirin, naproxen and indomethacin).

This therapeutic agent can be used in both veterinary medicine and in human therapy. For human therapy a preferred method of administering $\Delta^1$-THC-7-oic-acid would be orally in the form of a gelatin capsule. The dosage of the metabolite according to this invention generally is 10 to 500 mg/70 kilograms (kg) of body weight/day, preferably 50 to 150 mg/70 kg/day. The actual preferred amounts of active compound in a specific case will vary, of course, according to the particular species of mammal afflicted, the severity of the inflammation and the actual method of administration.

In addition to its analgesic and anti-inflammatory properties, THC is known to be useful as an antiemetic (especially against nausea and vomiting caused by cancer chemotherapeutic agents; Sallan, S. E., Cronin, C., Zelen, M. and Zinberg, N. E. *N. Eng. J. Med.*, 302:135–138, 1980) and as a bronchodilator for asthmatics. Thus, the metabolite, $\Delta^1$-THC-7-oic-acid, may possess these same properties. Furthermore, $\Delta^1$THC-7-oic-acid may be an effective therapeutic agent in treating fever because analgesic, anti-inflammatory and antipyretic properties are often associated with one another.

This invention has a further application in the area of medicinal chemistry where $\Delta^1$-THC-7-oic-acid can be used as a model to design similar or more efficacious synthetic analogs for relieving pain and tissue inflammation in mammals. An analog is a compound that resembles another in structure. For example, an analog of $\Delta^1$-THC-7-oic-acid may have a modification in one or more of the rings and one or more of its substituents alone or in combination.

The therapeutic agent of the present invention, or a synthetic analog thereof, can be administered to an afflicted mammal in the form of a composition comprising an analgesic and/or anti-inflammatory amount of $\Delta^1$-THC-7-oic-acid and a pharmacologically acceptable carrier therefor. Those skilled in the art will know, or will be able to ascertain with no more than routine experimentation, appropriate pharmacological carriers for said composition.

The invention is illustrated further by the following example, which is not to be taken as limiting in any way.

EXEMPLIFICATION

Chemicals

The THC used in these experiments was obtained from the National Institute on Drug Abuse. The metabolite, $\Delta^1$-THC-7-oic acid, was obtained from the Research Triangle Institute (Research Triangle Park, North Carolina). The purity of these cannabinoids was monitored by reversed phase thin-layer chromatography before experimentation. Naproxen, indomethacin, and carrageenan were purchased from Sigma Chemical Co. (St. Louis, Mo.).

The Mouse Hot Plate Test for Analgesia

The hot plate test is a method for measuring the analgesic activity of pharmacologic agents based on the reaction time of mice (Charles River CD-1) to lick their forepaws and/or jump after being placed on an aluminum hot plate heated and maintained at 54°–56° C. (Eddy, N. B. and Leimbach, D. J. *Pharmacol. Exp. Ther.* 107:385–393, 1953). A control reaction time (to the nearest 0.1 second) was obtained 3–4 hours before any test for drug effect. Groups of nine or ten mice were given various doses of either THC, $\Delta^1$-THC-7-oic-acid, naproxen, indomethacin or vehicle (control). All drugs were admininstered orally in a 40 ul volume of peanut oil. Sixty minutes later each mouse was re-exposed to the hot plate surface and the reaction times were recorded. The mean reaction time for the mice in each group was determined. The percent change of the mean reaction time when compared to predrug values is referred to as latency in Table I. (The probability values were derived from a paired t test.). This data demonstrates that the metabolite, $\Delta^1$-THC-7-oic-acid, exhibits analgesic activity with a potency similar to that of naproxen, one of the leading analgesic and anti-inflammatory agents in use today.

TABLE I

| The Mouse Hot Plate Test For Analgesia | | | | |
|---|---|---|---|---|
| Substance | Dose[1] | Latency | P[2] | N[3] |
| $\Delta^1$-THC | 40 | 51.3 | 0.0003 | 10 |
| $\Delta^1$-THC | 20 | 51.2 | 0.0044 | 10 |
| $\Delta^1$-THC | 10 | 29.5 | 0.107 | 10 |
| $\Delta^1$-THC | 5 | −10.2 | 0.180 | 10 |
| $\Delta^1$-THC-7-oic-acid | 40 | 52.7 | 0.019 | 9 |
| $\Delta^1$-THC-7-oic-acid | 20 | 53.0 | 0.023 | 10 |
| $\Delta^1$-THC-7-oic-acid | 10 | 21.7 | 0.16 | 10 |
| Naproxen | 80 | 60.6 | 0.0007 | 10 |
| Naproxen | 40 | 64.4 | 0.0012 | 10 |
| Naproxen | 10 | 26.9 | 0.025 | 10 |
| Indomethacin | 20 | 52.7 | 0.0067 | 9 |
| Indomethacin | 10 | 51.1 | 0.0025 | 9 |
| Vehicle | (40 ul) | 13.0 | 0.017 | 14 |

[1]mg/kg
[2]probability derived from a paired t test
[3]N = number of mice tested

The Mouse Carrageenan Edema Test

The basic experimental procedure was adapted from Sophia et al., *J. Pharma. Exper. Ther.* 186:646, 1973. Charles Rivier CD-1 female mice (20–25 g) were given a dose of either $\Delta^1$-THC-7-oic-acid, indomethacin or vehicle (control). All compounds were administered orally in a 20 ul volume of peanut oil. One hour later, 0.05 ml of a 1% solution of calcium carrageenan in saline was injected subcutaneously into the plantar surface of the right hind paw. The volume of the injected foot to the level of the lateral malleolus was measured by water displacement immediately before oral drug administration and again three hours after carrageenan injection. The difference between the two measurements was called edema volume. The effectiveness of each compound was analyzed in the following manner. For $\Delta^1$-THC-7-oic-acid, the mean paw volumes, before and after the metabolite was administered, were statistically compared by one-way ANOVA (analysis of variance) and Fisher PLSD Scheffe t-tests. For indomethacin, the mean paw volumes, pre- and postdrug, were statistically compared using the student's t-test. The percent inhibition of edema volume was obtained from the ratio of the predrug volume to the postdrug volume (Table II).

When administered in a dose of 40 mg/kg $\Delta^1$-THC-7-oic-acid inhibited edema by 79%. The results from this study clearly demonstrate the anti-inflammatory properties of $\Delta^1$-THC-7-oic-acid.

TABLE II

The Effect of $\Delta^1$-THC-7-Oic Acid and Indomethacin on Carrageenan-Induced Mouse Paw Edema

| Treatment | Dose[1] | Paw Volume[2] | N[3] | % Inhibition of Edema Volume |
|---|---|---|---|---|
| Vehicle | | 19 ± 19 | 18 | — |
| $\Delta^1$THC-7-oic-acid | 20 | 9 ± 12 | 10 | 53[4] |
| $\Delta^1$THC-7-oic-acid | 40 | 4 ± 13 | 15 | 79[4] |
| Indomethacin | 20 | −13 ± 17 | 10 | 100[5] |
| Vehicle | — | 35 ± 19 | 6 | — |

[1]mg/kg
[2]ul ± S.D.
[3]N = number of mice tested
[4]p = 0.030 determined by one-way ANOVA and Fisher PLSD and Scheffe t-tests
[5]p = 0.0001 determined by unpaired Student's t-test.

The Rat Ulcerogenicity Test

A quantitative assessment of experimentally induced acute gastric erosions and ulcers is crucial since their extent may be an indication of the ulcerogenic potential of pharmacologic agents (Robert and Szabo, 1983; Robert et al., 1979).

Experimental groups of 5-11 rats (Charles River CD) were fasted for 24 hours before the administration of either aspirin, $\Delta^1$-THC-7-oic-acid or indomethacin by a rubber stomach tube (Rusch No. 8). The animals were killed 1 hour later by carbon dioxide asphyxiation. At that time, 4 ml of 10% aqueous buffered formaldehyde (formalin) was injected directly into the stomach of each animal. This in situ intraluminal fixation with formalin was especially critical for the assessment of small gastric erosions induced by aspirin since the overlying hemorrhage could easily be removed by rinsing the unfixed stomach. After 5 minutes of in situ fixation, the stomach and proximal duodenum were removed, opened along the greater curvature, pinned on a cork with mucosa upward, and immersed in 10% formaldehyde until further processing (Szabo, S. et al, *J. Pharmacol. Meth.* 13:59–66, 1985). The gastric lesions were then evaluated by direct visual inspection.

For comparative purposes, a semiquantitative scale of 0–3 was used to assess the extent of gastric mucosal lesions (Scabo et al., 1981, 1983). According to this scale, a score of 0 indicates a normal mucosa; 1 represents the appearance of between 1 and 4 small petechiae; 2 indicates the presence of 5 or more petechiae or hemmorhagic streaks up to 4 mm in length; 3 represents the appearance of erosions longer than 5 mm or confluent hemorrhages.

The results from this study reveal that $\Delta^1$-THC-7-oic-acid, when directly administered in an amount representing 10 times the analgesic dose and 7–8 times the anti-inflammation and anti-pyretic doses of THC in the rat (50 mg/kg), does not induce the formation of gastric lesions (Table III). However, even when only half the therapeutic amount of aspirin (100 mg/kg) is administered each of the experimental animals experiences gastrointestinal damage.

TABLE III

The Rat Ulcerogenicity Test

| Substance | Dose[1] | Incidence[2] | Mean Score |
|---|---|---|---|
| Aspirin | 100 | 10/10 | 1.9 |
| $\Delta^1$-THC-7-oic-acid | 50 | 0/10 | 0.0 |
| Indomethacin | 20 | 6/11 | 0.77 |
| Indomethacin | 10 | 2/5 | 0.6 |

[1]mg/kg
[2]Number of rats with lesions/total tested

Equivalents

Those skilled in the art will recognize, or be able to ascertain using no more than routine experimentation, many equivalents to the specific embodiments of the invention described herein. Such equivalents are intended to be encompassed by the following claims.

I claim:

1. A method of relieving pain in a mammal comprising administering to said mammal an effective analgesic amount of $\Delta^1$-THC-7-oic acid or an analog thereof.

2. A method of claim 1 wherein the effective analgesic amount of $\Delta^1$-THC-7-oic acid or analog thereof is administered orally in the form of one or more gelatin capsules.

3. A method of claim 2 wherein said effective analgesic amount is a dosage of between about 10 mg/70 kg of body weight per day to about 500 mg/70 kg of body weight per day.

4. A method of claim 2 wherein said effective analgesic amount is a dosage of between about 50 mg/70 kg of body weight per day to about 150 mg/70 kg of body weight per day.

5. A method of relieving inflammation of bodily tissue in a mammal comprising administering to said mammal an effective anti-inflammatory amount of $\Delta^1$-THC-7-oic acid or an analog thereof.

6. A method of claim 5 wherein said effective anti-inflammatory amount of $\Delta^1$-THC-7-oic acid or analog thereof is administered orally in the form of one or more gelatin capsules.

7. A method of claim 6 wherein said effective anti-inflammatory amount is a dosage of between about 10 mg/70 kg of body weight per day and about 500 mg/70 kg of body weight per day.

8. A method of claim 6 wherein said effective anti-inflammatory amount is a dosage of between about 50 mg/70 kg of body weight per day and 150 mg/70 kg of body weight per day.

* * * * *